US008859513B2

(12) United States Patent
Sandino et al.

(10) Patent No.: US 8,859,513 B2
(45) Date of Patent: Oct. 14, 2014

(54) USE OF 1-BETA-D-RIBOFURANOSYL-1H-1,2,4-TRIAZOLE-3-CARBOXAMIDE FOR THE TREATMENT OF INFECTIOUS SALMON ANEMIA

(75) Inventors: Ana Maria Sandino, Santiago (CL); Geraldine Mlynarz Zylberberg, Santiago (CL); Matilde Jashes Morgues, Santiago (CL); Eugenio Spencer Ossa, Santiago (CL)

(73) Assignee: Laboratorio de Diagnostico Gam, S.A., Santiago (CL)

( * ) Notice: Subject to any disclaimer, the term of this patent is extended or adjusted under 35 U.S.C. 154(b) by 0 days.

(21) Appl. No.: 13/702,657

(22) PCT Filed: Jun. 8, 2010

(86) PCT No.: PCT/IB2010/052547
§ 371 (c)(1),
(2), (4) Date: Mar. 21, 2013

(87) PCT Pub. No.: WO2011/154771
PCT Pub. Date: Dec. 15, 2011

(65) Prior Publication Data
US 2013/0172284 A1    Jul. 4, 2013

(51) Int. Cl.
*A61K 31/70*     (2006.01)
*A01N 43/04*     (2006.01)
*A61K 31/7056*   (2006.01)

(52) U.S. Cl.
CPC .................................. *A61K 31/7056* (2013.01)
USPC .................... 514/43; 514/42; 514/45; 514/49

(58) Field of Classification Search
None
See application file for complete search history.

(56) References Cited

U.S. PATENT DOCUMENTS 7,652,050 B2 *    1/2010    Sandino et al. ............... 514/378

OTHER PUBLICATIONS

International Search Report for International Application No. PCT/IB2010/052547 mailed on Dec. 15, 2011.
Aspehaug et al., "Characterization of the Infectious Salmon Anemia Virus Fusion Protein," *Journal of Virology*, American Society of Microbiology, Oct. 2005, vol. 79, No. 19, pp. 12544-12553.
Barnard et al., "Enhancement of the infectivity of SARS-CoV in BALB/c mice by IMP dehydrogenase inhibitors, including ribavirin," *Antiviral Research*, Elsevier (2006), vol. 71, pp. 53-63.
Calligari et al., "Inhibition of viral group-1 and group-2 neuraminidases by oseltamivir: A comparative structural analysis by the ScrewFit algorithm," *Biophysical Chemistry*, Elsevier (2009), vol. 141, pp. 117-123.
Ergonul, O., "Treatment of Crimean-Congo hemorrhagic fever," *Antiviral Research*, Elsevier (2008), vol. 78(1), pp. 125-131.
Falk et al., "Demonstration of infectious salmon anaemia (ISA) viral antigens in cell cultures and tissue sections," *Veterinary Research*, Elsevier (1995), vol. 26, pp. 499-504.
Falk et al., "Characterization of Infectious Salmon Anemia Virus, an Orthomyxo-Like Virus Isolated from Atlantic Salmon (*Salmo salar* L.)," *Journal of Virology*, American Society of Microbiology, Dec. 1997, vol. 71, No. 12, pp. 9016-9023.
Falk et al., "Identification and Characterization of Viral Structural Proteins of Infectious Salmon Anemia Virus," *Journal of Virology*, American Society of Microbiology, Mar. 2004, vol. 78, No. 6, pp. 3063-3071.
Georges-Courbot et al., "Poly(I)-Poly($C_{12}$U) but Not Ribavirin Prevents Ddeath in a Hamster Model of Nipah Virus Infection,". *Antimicrobial Agents and Chemotherapy*, American Society of Microbiology, May 2006, vol. 50, No. 5, pp. 1768-1772.
Graci et al., "Mechanisms of action of ribavirin against distinct viruses," *Reviews in Medical Virology*, Wiley InterScience (2006), vol. 16, pp. 37-48.
Hong et al., "Pleiotropic mechanisms of ribavirin antiviral activities," *Progress in Drug Research*, Birkhäuser Verlag, Basel (Switzerland) (2002), vol. 59, pp. 41-69.
Hudson et al., "The efficacy of amantadine and other antiviral compounds against two salmonid viruses in vitro," *Antiviral Research*, Elsevier (1988), vol. 9, pp. 379-385.
Huggins, J, "Prospects for Treatment of Viral Hemorrhagic Fevers with Ribavirin, a Broad-Spectrum Antiviral Drug," *Reviews of Infectious Diseases*, May-Jun. 1989, vol. 11, Supplement 4, pp. S750-S761.
Jashés et al. "Inhibitors of infectious pancreatic necrosis virus (IPNV) replication," *Antiviral Research*, Elsevier (1996), vol. 29, pp. 309-312.
Jensen et al., "Effect of poly I:C on the expression of Mx proteins and resistance against infection by infectious salmon anaemia virus in Atlantic salmon," *Fish & Shellfish Immunology*, Elsevier Science Ltd. (2002), vol. 13, pp. 311-326.
Jonsson et al., "Treatment of hantavirus pulmonary syndrome," *Antiviral Research*, Elsevier B.V., Apr. 2008, vol. 78, No. 1, pp. 162-169.
Khan et al., "New opportunities for field research on the pathogenesis and treatment of Lassa fever," *Antiviral Research*, Elsevier (2008), vol. 78, pp. 103-115.
Kibenge et al., "Isolation and identification of infectious salmon anaemia virus (ISAV) from Coho salmon in Chile," *Diseases of Aquatic Organisms*, Inter-Research (2001), vol. 45, pp. 9-18.
Krossøy et al., "The Putative Polymerase Sequence of Infectious Salmon Anemia Virus Suggests a New Genus within the Orthomyxoviridae," *Journal of Virology*, American Society for Microbiology, Mar. 1999. vol. 73, No. 3, pp. 2136-2142.
Le et al., "Avian flu: Isolation of drug-resistant H5N1 virus," *Nature*, Nature Publishing Group, Oct. 2005, vol. 437, p. 1108.
Leyssen et al., "Molecular strategies to inhibit the replication of RNA viruses," *Antiviral Research*, Elsevier (2008), vol. 78, pp. 9-15.
Lovely et al., "First identification of infectious salmon anaemia virus in North America with haemorrhagic kidney syndrome," *Diseases of Aquatic Organisms*, (1999), vol. 35, pp. 145-148.

(Continued)

*Primary Examiner* — Patrick Lewis
(74) *Attorney, Agent, or Firm* — Merchant & Gould P.C.

(57) ABSTRACT

The invention relates to the novel use of 1-beta-D-ribofuranosyl-1H-1,2,4-triazole-3-carboxamide for the treatment of infectious salmon anaemia caused by the infectious salmon anaemia or ISA virus in salmonids.

5 Claims, 12 Drawing Sheets

(56) References Cited

OTHER PUBLICATIONS

Figure 1:
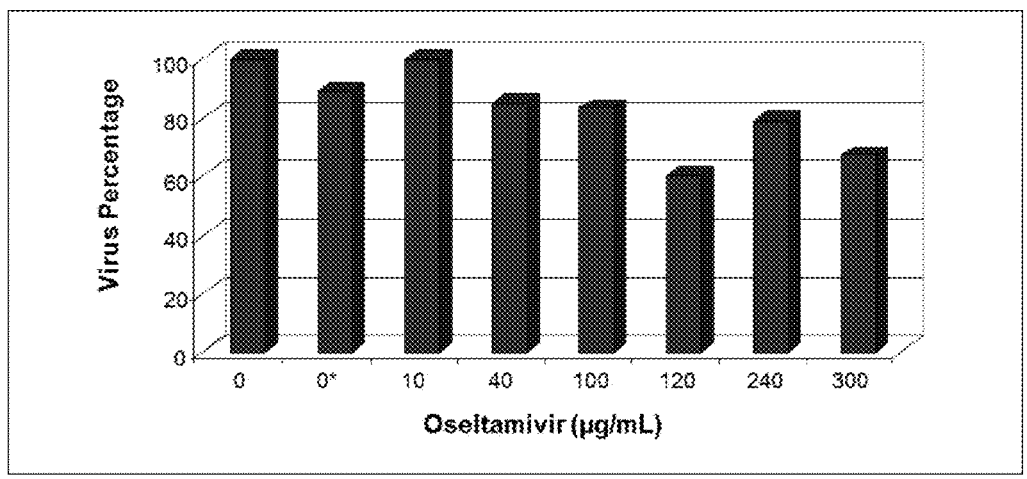
Figure 2:
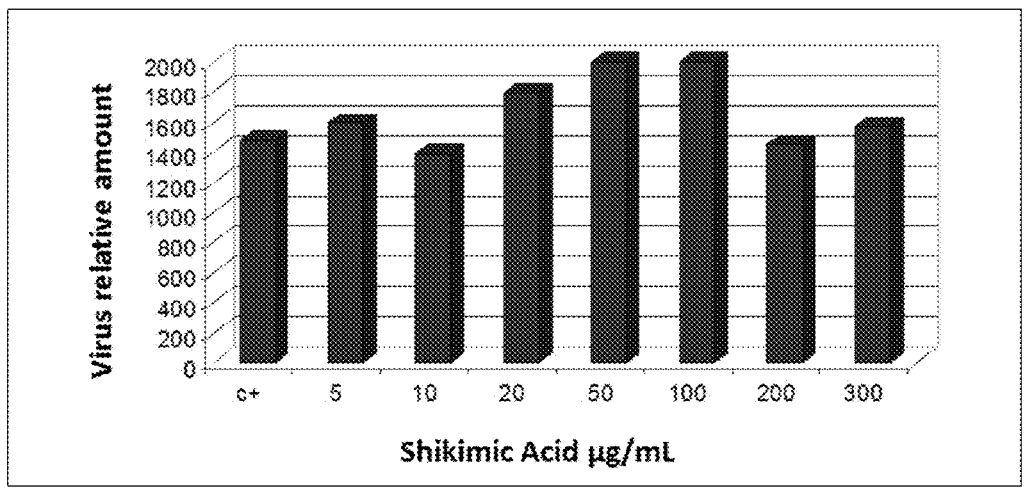
Figure 3:
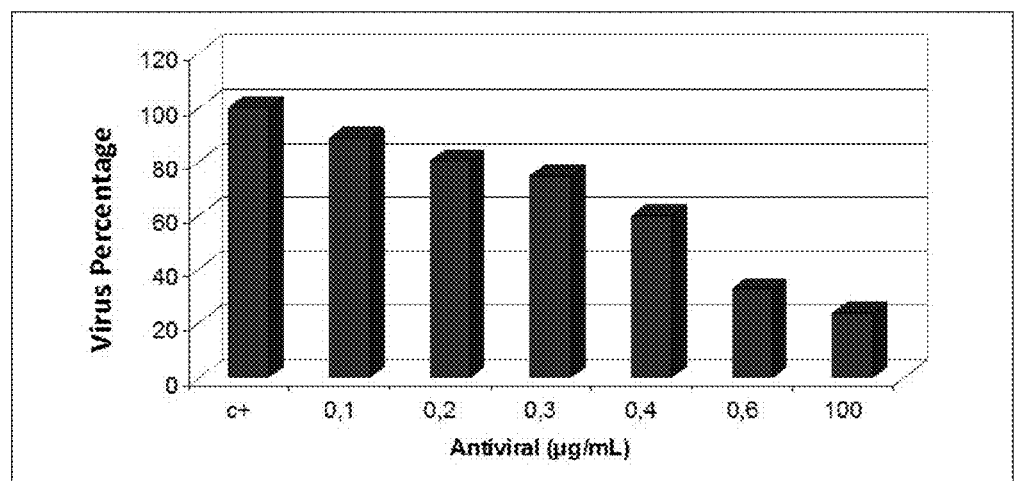
Figure 4:
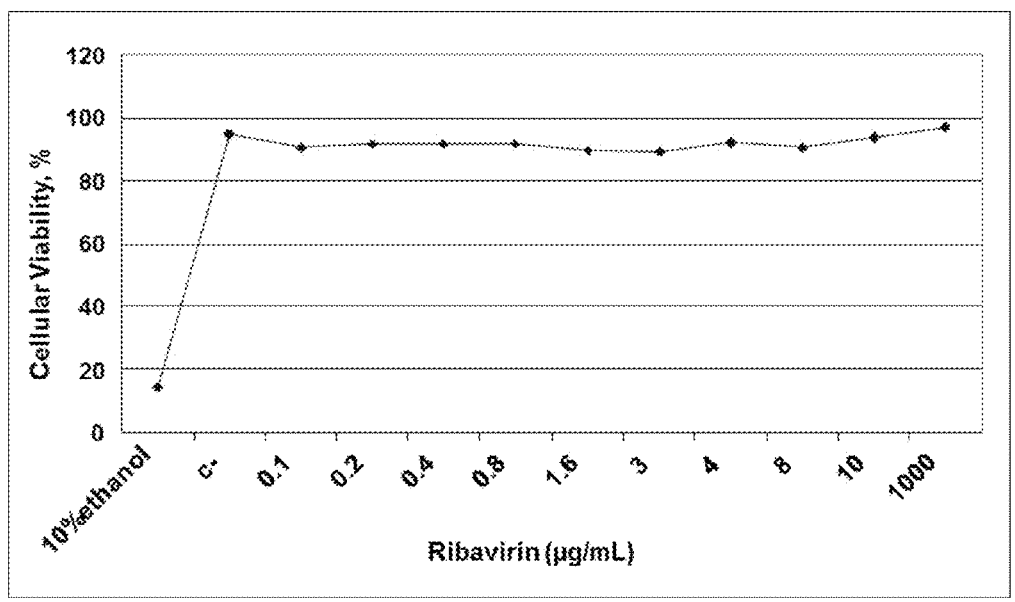

Marroquí et al., "Assessment of the inhibitory effect of ribavirin on the rainbow trout rhabdovirus VHSV by real-time reverse-transcription PCR," *Veterinary Microbiology*, Elsevier (2007), vol. 122, pp. 52-60.

Migus et al., "Effect of Ribavirin on the Replication of Infectious Pancreatic Necrosis Virus in Fish Cell Cultures," *Journal of General Virology*, (1980), vol. 47, pp. 47-57.

Munir, K et al., "Detection of infectious salmon anaemia virus by real-time RT-PCR," *Journal of Virological Methods*, Elsevier (2004), vol. 117, pp. 37-47.

Neyts et al., "Use of the yellow fever virus vaccine strain 17D for the study of strategies for the treatment of yellow fever virus infections," *Antiviral Research*, Elsevier (1996), vol. 30, pp. 125-132.

Saijo et al., "Inhibitory effect of mizoribine and ribavirin on the replication of severe acute respiratory syndrome (SARS)-associated coronavirus," *Antiviral Research*, Elsevier (2005), vol. 66, pp. 159-163.

Savan et al., "Effect of virazole on rainbow trout *Salmo gairdneri* Richardson fry infected with infectious pancreatic necrosis virus," *Journal of Fish Diseases*, Blackwell Scientific Publications (1980), vol. 3, pp. 437-440.

Severson et al., "Ribavirin Causes Error Catastrophe during Hantaan Virus Replication," *Journal of Virology*, American Society for Microbiology, Jan. 2003, vol. 77, No. 1, pp. 481-488.

Thorud et al., "Infectious Anaemia in Atlantic Salmon (*Salmo salar* L.)," *Bull Eur Assoc Fish Pathol*, (1988), vol. 8, No. 5, pp. 109-111.

Watts et al., "Inhibition of Crimean-Congo Hemorrhagic Fever Viral Infectivity Yields in Vitro by Ribavirin," *The American Journal of Tropical Medicine and Hygiene*, The American Society of Tropical Medicine and Hygiene (1989), vol. 41, No. 5, pp. 581-585.

Hellebø et al., "Infectious Salmon Anemia Virus Specifically Binds to and Hydrolyzes 4-O-Acetylated Sialic Acids," *Journal of Virology*, American Society of Microbiology, (2004) vol. 78, No. 6, pp. 3055-3062.

Jorgensen et al., "Gene expression analyses in Atlantic salmon challenged with infectious salmon anemia virus reveal differences between individuals with early, intermediate and late mortality," *BMC Genomics*, (2008) vol. 9, pp. 179-194.

Mjaaland et al., "Susceptibility and immune responses following experimental infection of MHC compatible Atlantic salmon (*Salmo salar* L.) with different infectious salmon anaemia virus isolates," *Archives of Virology*, (2005) vol. 150, pp. 2195-2216.

Snell, N. J. C., "Letter to the Editor: Ribavirin Therapy for Nipah Virus Infection," *Journal of Virology*, American Society for Microbiology, (2004) vol. 78, No. 18, p. 10211.

Totland et al., "Transmission of infectious salmon anaemia (ISA) through natural secretions and excretions from infected smolts of Atlantic salmon *Salmo salar* during their presymptomatic phase," *Diseases of Aquatic Organisms*, (1996) vol. 26, pp. 25-31.

\* cited by examiner

USE OF 1-BETA-D-RIBOFURANOSYL-1H-1,2,4-TRIAZOLE-3-CARBOXAMIDE FOR THE TREATMENT OF INFECTIOUS SALMON ANEMIA

This application is a National Stage Application of PCT/IB2010/052547, filed 8 Jun. 2010 and which application is incorporated herein by reference. To the extent appropriate, a claim of priority is made to the above disclosed application.

DESCRIPTION OF THE INVENTION

The present invention relates to the novel use of ribavirin for the treatment of infectious salmon anemia caused by the infectious salmon anemia or ISA virus in salmonids.

BACKGROUND OF THE INVENTION

Infectious Salmon Anemia (ISA) is a viral exclusive in culture disease of the Atlantic salmon (*Salmo salar* L.), discovered in 1984 in Norway (Thorud and Djupvik, *Infectious anemia in Atlantic salmon (Salmo salar* L.), *Bull. Eur. Assoc. Fish Pathol.* 8: 109-111, 1988) and it is characterized by provoking high mortality in fish. The most common signs are severe anemia; exophthalmos; ascites; petechial hemorrhage in viscera, adipose tissue and skin; and hemorrhagic necrosis in the liver of infected fish (Falk and Dannevig, *infectious salmon anemia Demonstration of (ISA) viral antigens in cell cultures and tissue sections. Vet. Res* 26: 499-504, 1995; Falk et al, *Characterization of infectious salmon anemia virus, an orthomyxo-like virus isolated from Atlantic salmon (Salmo salar* L.), *J. Virol.* 71: 9016-9023, 1997, Munir and Kibenge, *Detection of infectious salmon anemia virus by real-time RT-PCR. J. Virol. Methods* 117: 37-47, 2004). In the economic field, this disease has caused great losses in salmon producing countries where it has been declared, such as Norway, Canada, Scotland, Faroe Islands and the United States (Kibenge et al, *Isolation and identification of infectious salmon anemia virus (ISAV) from Coho salmon in Chile, Dis Aquat Organ* 45, 9-18, 2001; Lovely et al, *First identification of infectious salmon anemia virus in North America with haemorrhagic kidney syndrome, Dis Aquat Organ* 35, 145-148, 1999; Falk and al, *Identification and characterization of viral structural proteins of infectious salmon anemia virus, J Virol* 78, 3063-3071, 2004). Moreover, in the case of Norway, the high mortality produced losses covering almost the entire production, reporting up to 80% reductions in the total production of the country. Chile, a country that until recently was free of the disease, has also been attacked by the virus, partly due to the globalization of markets and on the other hand due to the intense production conditions at the farms, which allows an easy dissemination, representing a problem often difficult to control. Finally the pathogen agent was first detected in Chile in 2001 (Kibenge et al, *Isolation and identification of infectious salmon anemia virus (ISAV) from Coho salmon in Chile, Dis Aquat Organ* 45, 9-18, 2001).

The etiologic agent of this disease is the Infectious Salmon Anemia Virus (ISAV). It belongs to the Orthomyxoviridae family, it has 8 segments of single-stranded genomic RNA of negative polarity, coding for 8 structural proteins and 2 non-structural proteins. The genomic organization of ISAV has situated it in a new genus, the Isavirus or Aquaorthomyxovirus (Krossoy et al, *The putative polymerase sequence of infectious salmon anemia virus Suggests a new genus Within the Orthomyxoviridae, J Virol* 73, 2136-2142, 1999). The 8 genomic RNA segments are attached to multiple copies of the viral nucleoprotein (NP), a copy of the RNA polymerase complex formed by proteins PB1, PB2 and PA is situated at the ends 3'; which altogether are called ribonucleoproteins. A membrane envelope in which the glycoproteins Hemagglutinin-esterase (HE) and fusion (F) are inserted surrounds the protean capsid, which is formed by matrix protein M1 and M2, (Aspehaug et al, *Characterization of the infectious salmon anemia virus fusion protein, J Virol* 79, 12544-12553, 2005).

The ISAV replicative cycle is very similar to the influenza A virus, where the HE protein identifies a cellular receptor containing 4-O-acetyl-sialic acid (Hellebo et al, *Infectious salmon anemia virus binds to and hydrolyzes especificamente 4-O-acetylated sialic acids, J Virol* 78, 3055-3062, 2004). Subsequently the particle is entered into the cell in vessels covered with clathrin, which are fused to endosomes, providing the necessary acidic environment for the fusion among membranes, both viral and endosomal, allowing the stripping of the virus. The viral ribonucleoproteins are forwarded to the nucleus of the cell, where viral transcription starts. The viral mRNA produced at the nucleus is translated in the cellular cytoplasm, returning to the nucleus only the NP, PB1, PB2 and PA proteins; allowing the beginning of viral replication and subsequently, the formation of ribonucleoproteins. The assembly of mature viral particles is performed in the cell membrane toward which the glycoproteins are headed, HE and F, and also M proteins, which will be the NP receptors, finally releasing the virions by a budding process.

The study of diseases caused by microorganisms allows the design of different control strategies, either with early diagnosis, confronting the spread of the disease or mainly attacking its origin, that is, the same microorganisms. In the case of virus, it is essential to study both the replicative cycle in general and the function and structure of each of the viral proteins. Through these studies it has been found that the orthomyxovirus undergoes a high rate of mutation and recombination forming new strains from one year to another. This is the main reason why prevention through vaccination does not guarantee protection against infection with these agents, leading to develop alternative therapies to prevent the spread of infection within and between organisms. The design and testing of compounds that interfere with the replication cycle of the virus is a relevant area of study for the control of the orthomyxovirus as ISAV.

To date, approximately 40 antiviral compounds have been approved for its use in humans, primarily for the treatment of infections caused by the human immunodeficiency virus (HIV), hepatitis B virus (HBV) and herpes virus. On the other hand, the number of approved antiviral compounds that can be used for the treatment of infections caused by RNA is limited. Among these are, without considering treatment for HIV, the M2 channel inhibitors, amantadine and rimantadine, and the neuraminidase inhibitors, oseltamivir and zanamivir for influenza; and ribavirin for the treatment of respiratory syncytial virus (RSV), the hepatitis C virus (HCV) and is also being used for the treatment of Lassa fever (Revised In: Leyseen et al, *Molecular Strategies to inhibit the replication of RNA viruses, Antivir. Res* 78: 9-15, 2008).

Ribavirin is a synthetic nucleoside whose chemical name is 1-beta-D-ribofuranosyl-1H-1,2,4-triazole-3-carboxamide having the following structural formula (Formula I):

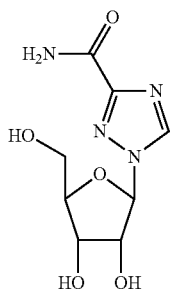

Formula I

Ribavirin is a broad-spectrum inhibitor of RNA virus replication, which has been approved for treatment of HCV infections in combination with interferon and for the treatment of RSV infections in pediatric aerosol form. It has also been used experimentally for other conditions, including Lassa fever (Khan et al, *New Opportunities for field research on the pathogenesis and treatment of Lassa fever, Antivir. Res* 78: 103-115, 2008), CCHF virus (Ergonul, *Treatment of Crimean-Congo hemorrhagic fever. Antivir res* 78: 125-131, 2008) and Hantavirus (Jonsson et al. *hantavirus pulmonary syndrome Treatment of, Antivir. res* 78: 162-169, 2008). While it has been found that the compound inhibits in vitro replication of some viruses studied, most of them being RNA virus, it has been shown to have a protective effect only in some animal models. Also, the power of the in vitro activity of ribavirin may vary considerably depending on the nature of the virus (Graci and Cameron, *Mechanism of action of ribavirin against distinct viruses, Rev. Med. Virol.* 16, 37-48, 2006).

It has been reported that most of RNA viruses are sensitive to the activity of ribavirin in vitro, but only some of them are more susceptible than others. In general, ribavirin is not very potent as an antiviral medication regularly showing EC50 values (effective concentration 50%) of 1 µM or even higher. Specifically, in vitro antiviral activity has been proved against bunyaviruses including CCHF virus (hemorrhagic fever Crimean-Congo), Rift Valley fever virus, and Hantavirus. It also inhibits the replication of coronaviruses, including coronavirus-SARS and flaviviruses, but has shown not to be effective in animals experimentally infected with these viruses (Watts y cols, *Inhibition of Crimean-Congo hemorrhagic fever viral infectivity yields in vitro by ribavirin. Am. J. Trop. Med. Hyg.* 41: 581-585, 1989; Huggins, *Prospects for treatment of viral hemorrhagic fevers with ribavirin, a broad-spectrum antiviral drug. Rev. Infect. Dis.* 11 (Suppl. 4) S750-S761, 1989; Severson y cols, *Ribavirin causes error catastrophe during Hantan virus replication. J. Virol.* 77: 481-488, 2003; Saijo y cols, *Inhibitory effect of mizoribine and ribavirin on the replication of severe acute respiratory syndrome (SARS)-associated coronavirus. Antivir. Res.* 66: 159-163, 2005; Barnard y cols, *Enhancement of the infectivity of SARS-CoV in BALB/c mice by IMP dehydrogenase inhibitors, including ribavirin. Antivir. Res.* 71: 53-63, 2006; Neyts y cols, *Use the yellow fever virus vaccine strain 17D for the study of strategies for the treatment of Bellow fever virus infections. Antivir. Res.* 30 (2-3): 125-132, 1996). At a similar way, ribavirin is not effective in animal models infected with filovirus (Huggins, *Prospects for treatment of viral hemorrhagic fevers with ribavirin, a broad-spectrum antiviral drug. Rev. Infect. Dis.* 11 (Suppl. 4) S750-S761, 1989). It has also been observed that ribavirin is effective in vitro and in vivo against RSV, a paramyxovirus, and it reveals relative sensitivity in cell cultures of other paramyxoviruses, the Nipah virus, but only limited efficacy in animals models has been observed (Snell, *ribavirin therapy for Nipah virus infection. J. Virol.* 78: 10211, 2004, Georges-Courbot et al, *Poly-(I)-poly (C12U) but not ribavirin prevents it death in a hamster model f Nipah virus infection. Antimicrob. Agents Chemother.* 50: 1768-1772, 2006).

It has also been evaluated the effect of ribavirin on VHSV virus (Viral Hemorrhagic Septicemia Virus), in EPC cell cultures (*Ephitelioma papulosum cyprini*). Cells were infected with the virus and treated with 1 to 25 µg/ml Ribavirin. The results revealed a strong inhibition of the virus at concentrations of 5, 10 and 25 µg/ml. They also show a high inhibition of viral RNA accumulation when 25 µg/ml are added at 0 hours post infection, occurring RNA inhibition of 99.8% at 10 hours post infection. This report concludes that the measuring method employed (RT-PCR in real time) can be used in combination with the classical methods to study the progression of the infection and the kinetics of virus replication, but there is however, not always a correlation of in vitro results with the protection given to the fish, so it is necessary to conduct tests in vivo (Moroccan et al., *Assessment of the inhibitory effect of ribavirin on the rainbow trout rhabdovirus VHSV by real-time reverse-transcription PCR, Vet. Microbiol.* 122: 52-60, 2007). In this case, a test was conducted with a virus that infects the rainbow trout and its effect in vitro was assayed. There are no reports in vivo and not anything suggests that the same effects on cells in culture could be seen in fish.

On the other hand the antiviral effect of ribavirin in cell cultures infected with IPNV virus (Infectious Pancreatic Necrosis Virus) has been evaluated (Jashés et al. *Inhibitors of infectious pancreatic necrosis virus (IPNV) replication, Antiviral Res* 29: 309-312, 1996, Hudson et al, *The Efficacy of amantadine and other antiviral compounds against salmonid two viruses in vitro, Antiviral Res* 9: 379-385, 1988). It was observed that this antiviral is capable of inhibiting viral replication in vitro of the IPN virus with an EC50 of 0.5 g/mL and a $CC_{50}$ of 100 µg/mL, but it was not the most effective antiviral and the in vivo activity was no longer evaluated (Jashés et al. *Inhibitors of infectious pancreatic necrosis virus (IPNV) replication, Antiviral Res* 29: 309-312, 1996).

In an in vivo study reported in 1980, the effect of ribavirin on IPNV infected rainbow trout was analyzed. The compound was supplied through a solution in the tank where the fish were held by exposure to the antiviral once during two hours. The administration was performed in increasing concentrations to the fish into two separate batches of 6 tanks each. The results revealed a decreased rate of dead fish in about 5%, but there was not a linear effect over the concentration of the antiviral used. Also the higher dose of ribavirin administered, 400 µg, produced no greater decrease in the rate of death. It is concluded that higher doses of ribavirin do not produce a greater decrease in the quantity of dead fish. An alternative treatment option would be a sustained exposure to antiviral in order to decrease significantly the death rate of infected fish. However it is suggested that the costs involved would be very expensive and most fish farm owners would be hostile to initiate any antiviral treatment before the existence of an apparent viral illness (Sayan and Dobos. *Effect of Virazole on rainbow trout fry Salmo gairdneri Richardson infected with infectious pancreatic necrosis virus, J. Fish Dis.*, 3: 437-440, 1980). No further testing is reported, so that the usefulness of ribavirin in the treatment of IPNV infected trout has not been demonstrated.

There have been several proposals of molecular mechanisms responsible for the antiviral activity of ribavirin (Hong and Cameron, *pleiotropic Activities Mechanisms of antiviral*

*ribavirin, Prog Drug Res* 59: 41-69, 2002; Revised: Leyseen et al, *Molecular Strategies to inhibit the replication of RNA viruses, Antivir. Res* 78: 9-15, 2008). These mechanisms include: (1) depletion of intracellular levels of GTP by inhibition of intracellular IMP dehydrogenase caused by 5'-monophosphate metabolite of ribavirin, (2) inhibition of the viral polymerase activity, caused by the 5'-triphosphate metabolite of ribavirin, (3) inhibition of the viral capsid through inhibition of the guaniltransferase activity caused by the 5'-triphosphate ribavirin, (4) inhibition of viral helicase causing the process known as catastrophic error resulting of the accumulation of mutations, some of them being lethal, in the viral genome.

In the present, it is still in debate the magnitude of the contribution of the catastrophic error, of the depletion of intracellular levels of GTP and other proposed mechanisms of antiviral activity of ribavirin, and the way they would contribute in the in vivo activity of this antiviral.

As it has already been mentioned, ribavirin is used in the chronic treatment of hepatitis C in humans, in association with interferon alpha. The information available for the product Rebetol®, containing ribavirin as active ingredient, establishes that the FDA (Food and Drug Administration) alerts about an important primary toxicity of this compound, because it triggers hemolytic anemia in patients treated with the product and can lead to a worsening of cardiac disease causing both fatal and non-fatal myocardial infarction.

Figure 18:
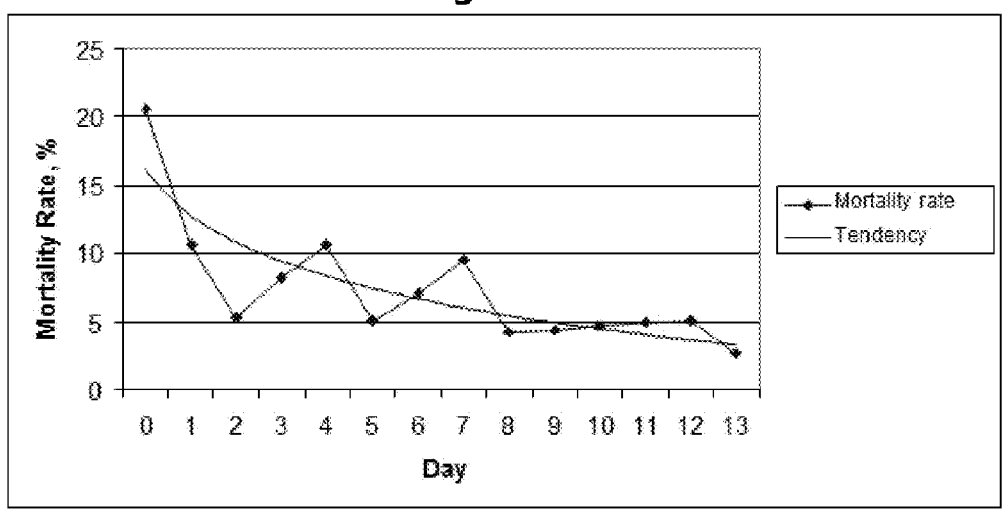

From the available information the need for a treatment for fish infected with ISA virus is required. It is in fact a problem in the aquaculture farms, and there is no currently an effective and efficient solution, that would arrest and reverse infections caused by these viruses. If is not arrest, they could cause great economic losses and producers and consumers will be affected significantly.

The fact of the need of an effective and efficient treatment is also related to its cost, so as not to increase the price of the final product, in order to give the possibility to dispense a product not only when the disease has spread but also, and as it has been suggested for other pathologies treated with antiviral drugs, to be able to dispense it in the early stages of infection, thus allowing more protection by reducing the propagation of the replication stage in which the virus is. This would prevent healthy fish from being infected by cohabitation, blocking the spread and eventually stopping the disease.

From the available data, there is not a compound capable of inhibiting the ISA virus and even more that could do it in vivo, or in naturally infected fish.

As it has been mentioned previously, considering the high mutation presented by the ISA virus that leads to a change in vaccines every year because the effectiveness decrease, the problem should be addressed by looking at the properties of the etiologic agent remaining in time and that are vulnerable to other mechanisms. In view of the ISA virus shares certain characteristics with the influenza virus, the inventors concluded that an efficient way to control the disease could be use of known efficient antivirals to inhibit these viruses. But surprisingly, inventors found that out of all antiviral tested, only ribavirin showed to be really effective in vitro.

Ribavirin is a broad-spectrum antiviral compound, but the background and the available data do not suggest that it might be useful for the treatment of this disease, even more considering that it has been reported that one of its most important toxic effects is hemolytic anemia. An expert in the art would never even think about using it for the treatment of an infection caused by ISAV, disease characterized by the development of severe anemia, among other complications, which altogether are ultimately fatal to the fish.

Contradicting all predicted ideas, the inventors of the present invention have surprisingly found that ribavirin is effective in the treatment of fish infected with ISA virus.

BRIEF DESCRIPTION OF THE INVENTION

The present invention relates to the novel use of ribavirin for the treatment of infected fish by the virus of infectious salmon anemia or ISAV. Ribavirin will be referred to hereinafter as such or as "Antiviral".

DESCRIPTION OF THE FIGURES

FIG. 1: Viral viability in different concentrations of oseltamivir.

FIG. 2: Viral viability in different concentrations of shikimic acid.

FIG. 3: Viral viability in different concentrations of antiviral.

FIG. 4: Cell viability in different concentrations of antiviral.

FIG. 5: Cumulative Mortality in fish treated with the antiviral in different oral doses. This figure shows the cumulative mortality observed in the 5 tanks of the test. Fish in tanks C1, C2 and C3 are controls that did not receive antiviral. The fish in tanks T1 and T2 received doses of 800 μg/mL and 400 μg/mL of the compound.

FIG. 6: Total average viral load after of the fish treatments in tanks C3, T1 and T2.

FIG. 7: Average viral load in live fish samples. These fish were killed by euthanasia at the end of the assay. Viral loads of tanks C3, T1 and T2 are shown.

FIG. 8: Average viral load in dead fish samples from the tanks C3, T1 and T2. These fish died during the assay by ISA virus.

FIG. 9: Average viral load in infected fish samples from the tanks C3, T1 and T2. These fish were infected by intraperitoneal injection.

FIG. 10: Viral load in uninfected fish samples from the tanks C3, T1 and T2. These fish were infected by cohabitation with intraperitoneally pre-infected fish.

11A and 11B: Photograph of necropsy in fish of the tank C1.

12A and 12B: Photograph of necropsy in fish of the tank C2.

FIG. 13 A: Photograph of necropsy in fish of the tank C3.

FIG. 13 B: Close-Up of the photography of necropsy of the FIG. 13 A.

FIG. 14 A: Photograph of necropsy of a fish of the tank T1 intraperitoneally infected by ISA virus. This fish was treated with 800 μg/mL Antiviral.

FIG. 14 B: Photograph of necropsy of two fish of the tank T1 infected by cohabitation with ISA virus. This fish was treated with 800 μg/mL Antiviral.

FIG. 15 A: Photograph of necropsy of a fish of the tank T2 intraperitoneally infected by ISA virus. This fish was treated with 400 μg/mL Antiviral.

FIG. 15 B: Photograph of necropsy of a fish of the tank T2 infected by the virus ISA cohabitation. This fish was treated with 400 μg/mL Antiviral.

FIG. 16: Average hematocrit. The hematocrit in fish of the tanks C1, C2, C3, T1 and T2 is shown.

FIG. 17: Viral load in vivo. The fish viral load of 2.5 kg naturally infected by ISA virus and treated intraperitoneally with 400 mg/kg Antiviral is shown.

FIG. 18: Daily Mortality rate. The fish mortality rate of 2.5 kg which received a single dose of 400 mg/kg Antiviral on day 0 is shown.

DETAILED DESCRIPTION OF THE INVENTION

Inhibition Assays of Viral Replication

SHK-1 Cell Culture

The SHK-1 cells derived from the Atlantic salmon kidney were grown at 15° C. in growth medium (Medium Leibovitz L-15, 4 mM L-glutamine, 40 mM 2-mercaptoethanol, 50 mg/mL gentamicin sulfate, 8% SFB).

ISA Virus Spread

Monolayers of SHK-1 cells grown for 3 days up to a confluence of 60% approximately, were inoculated with a 1/10 dilution of a virus isolated in a culture of SHK-1 cells from the heart of a naturally infected fish in southern Chile, in infection medium (Leibovitz L-15 without FBS, 4 mM L-glutamine, 40 mM 2-mercaptoethanol, 50 µg/mL gentamicin). After 4 hours of incubation at 15° C. the inoculum was replaced by growth medium. Infected monolayers were incubated afterwards at 15° C. for 3 days. The presence of ISA virus in the inoculum was checked by RT-PCR in real time.

Inhibition Assay of the Replicative Cycle of ISAV

Monolayers of SHK-1 cells were grown in 6-well plates, 9.6 cm². The cells were propagated by no more than 3 days and were infected with ISAV. After 4 hours of incubation with virus, the medium was replaced by growth medium including various dilutions of different compounds to be tested (Antiviral, oseltamivir or shikimic acid). After 3 days of post-infection the cell supernatant was collected and subjected to extraction of viral RNA. Viral replication was qualitatively analyzed with RT-PCR quantification in real time.

Viral viability was assessed in cells infected with ISA virus, in different antiviral concentrations proved to be effective in the influenza treatment. It was observed that both oseltamivir, a well-known antiviral used in the treatment of influenza, as its precursor, shikimic acid, were little effective in inhibiting viral replication. In the case of oseltamivir no more than 60% of inhibition was obtained for the replication of ISA virus in concentrations as high as 300 µg/mL (FIG. 1). On the other hand for influenza viruses A and B, $EC_{50}$ ranging from 0.03 ng/mL to 2.84 ng/mL have been reported (Mai Le et al, *Isolation of drug-resistant H5N*1 *virus, Nature* 437: 1108, 2005 Calligari et al, *Inhibition of viral Group*-1 *and Group*-2 *neuraminidases by oseltamivir: A comparative structural analysis by the ScrewFit algorithm, Biophys. Chem* 141: 117-123, 2009).

The results obtained with the shikimic acid were less promising, since there was no viral replication inhibition up to concentrations of 300 μg/ml (FIG. 2). This also shows that no a correlation between the amount of virus and doses of compound tested.

These results demonstrate that even though the antiviral can be effective for certain viruses, it does not mean that is true for other related viruses, not even under appropriate in vitro conditions.

Otherwise, by subjecting the cells infected with ISA virus at different concentrations of the antiviral (ribavirin), an inhibition of virus replication was observed, which increased as the compound concentration was increased (FIG. 3). The concentration which inhibits 50% of ISA virus replication ($EC_{50}$) was about 0.4 μg/ml. This means that at fairly low concentrations of Antiviral an effective inhibition of virus replication is obtained.

As already discussed, a positive result in the in vitro inhibition for ISAV does not suggest that the compound is effective for the treatment of disease caused by the same virus in fish.

Determination of Toxicity

The cytotoxicity of the compounds was assessed by cell viability assays. All assays were performed in SHK-1 cell cultures in duplicate.

In order to evaluate the cytotoxic effect of antiviral compounds on cell viability, monolayers of SHK-1 cells were grown in culture individual wells of 9.6 $cm^2$, up to a confluence of about 90-100%. In order to obtain a constant number of cells or a culture in growth steady state, fetal bovine serum (FBS) was removed from the culture medium. To each well a solution of the antiviral compound at different concentrations was added. Cells were incubated for 3 days at 15° C. The state of the cell monolayer was observed in the inverted light microscope. The cells were subsequently washed twice with PBS, and then sprung with 200 μL of 0.5 mM EDTA and 0.02% trypsin and incubated for 2 minutes at room temperature. The cells were centrifuged for 10 minutes at 3000 rpm, the supernatant removed and re-suspended in PBS 2% FBS. 3 μL propidium iodide (50 μg/mL in phosphate buffer) were added to 200 μL of cell suspension and a cytometric counting of the viable and nonviable cells of a total of 100,000 cells was performed. The result was expressed as percentage of living cells (% cell viability).

FIG. 4 shows the effect of increasing concentrations of Antiviral (ribavirin) on cell viability. The cells remained intact, close to 100% up to a concentration of at least 1 mg/mL Antiviral.

In these experiments, it was found that the concentration that produces 50% of cell toxicity ($CC_{50}$) was upper than 400 mg/mL, a valor much higher than the $EC_{50}$ values found (FIG. 3).

With these results is not yet possible to ensure that the antiviral is effective in the treatment of disease caused by the ISA virus in salmonids, because while it is very promising that the compound efficiently inhibits viral replication in vitro and does not have cytotoxicity in concentrations up to $10^7$ times higher than the actual, it is not possible to extrapolate its utility in vivo.

Since ribavirin is approved for use in humans by international regulatory agencies, such as Food and Drug Administration of the United Sates (FDA) and the European Medicines Agency (EMA), it is possible to guarantee some security for its use in fish.

Evaluation of the Antiviral Effect of Ribavirin in Smolt Fish

Tests were conducted in a controlled seawater environment (25 ppt) with 156 units of smolt fish from the *Salmo salar* specie of about 70 g in weight, at the Universidad Católica de la Santísima Concepción de Chile.

The fish were distributed into its respective tanks and were left for 7 days to acclimatize before performing the process of infection. Fish were distributed in 5 independent systems with recirculating seawater, with two culture tanks, of 140 liters each one. Each line had a collector tank that distributed water to the closed system, and a biological filter to control nitrogen compounds.

The collector tank had a minimum capacity of 40 liters, from which the water is distributed to each of the tanks within the line. The tank should maintain conditions of pH, ammonium, and normal oxygenation accepted regularly by farms. The water distribution flow to the lines is consistent with a recirculation rate of 2 to 4 times/hour and a renewal rate of 10 to 30% of fresh water per day.

The temperature was kept between 14 to 16° C. Abiotic factors such as pH and ammonia concentration were those normally accepted in Recirculating Systems of fish farms and were monitored with a biological filtration system.

The water circulation from the collector to the tanks was kept constant, maintaining a water recirculation rate of 2 to 4 times/hour, and was kept at the same rate between the tanks.

The fish were fed with 0.5% of their body weight of medicated feed or control feed.

After acclimatization they were separated into two groups of 30 fish each that remained uninfected. The first being the healthy control group (C1, see Table 2) and the second was the healthy control group treated with the highest antiviral dose (to assess toxicity) (C2, see Table 2).

The remaining 96 fish were divided into three groups of 32 fish each, and were placed in separate tanks termed C3, T1 and T2. 40% of the fish from each of these tanks were injected intraperitoneally with a suspension of ISA virus and the remaining 60% were expected to get the infection by cohabitation. Thus the experimental infection resembles the reality at the farming.

The material that was in contact with the fish as thermometers, vacuum hoses, nets to move the fish, was properly separated and to each working group a set of exclusive use material was assigned.

Two of the three groups of infected fish were treated with the antiviral compound for 10 consecutive days (T1 and T2, see Table 2) and the other group was the untreated infected control group (C3). The treatment was started on day 11 post-infection and was provided with food. 2 doses of antiviral compound mixed with the feed were tested and also the excipient without the antiviral mixed with food.

Because 30 small fish were distributed per tank, with an average weight of 70 g, and that only 0.5% of body weight of medicated feed would be provided, the fish were not given normal food, in order to ensure that all supplied food would be ingest by them.

Preparation of Medicated Feed:

Formulations of the antiviral were made available in order to prepare the medicated feed, as shown in the following Table 1:

TABLE 1

Powder Formulations for oral administration of Ribavirin

| Description | % | Theorical amount (g) | Weighed amount (g) |
|---|---|---|---|
| Ribavirin base | 0.5-5 | 0.5-5 | 0.75-7.5 |
| *Starch 1500 | 99.5-95 | 99.5-95 | 149.25-142.5 |
| TOTAL | 100 | 100 | 150 |

*Partially pregelatinized corne starch

Four types of medicated feed were prepared, they are termed: Feed F1, Feed F2, Feed F3 and Feed F4.

Feed F1: (400 μg/kg) 0.084 g of 1% Antiviral formulation was mixed with 10.21 g of food. The mixture was vigorously stirred in an inflated polyethylene bag and then 0.210 mL of vegetable oil was added. It was stirred again until complete homogenization.

Feed F2: (800 μg/kg) The same procedure as F1 was used but adding 0.168 g of 1% Antiviral formulation.

Feed F3: (1,600 μg/kg) The same procedure as F1 was used but adding 0.336 g of 1% Antiviral formulation.

Feed F4: 0.336 g of the excipients used in the formulations of the antiviral powder were weighted and mixed with 10.21 g of food. After vigorously stirring in an inflated polyethylene bag, 0.210 ml of vegetable oil were added. It was stirred again until complete homogenization.

The experimental design is summarized in the following Table 2:

TABLE 2

Distribution of different assays and its encodings are listed.

| Tanks | Treatment | Antiviral dose (μg/kg) | Medicated feed | Duration of treatment (days) | Fish amount |
|---|---|---|---|---|---|
| C1 | Healthy control | 0 (only excipients) | F4 | 10 | 30 |
| C2 | Healthy control + oral treatment | 1600 | F3 | 10 | 30 |
| C3 | Infected control | 0 (only excipients | F4 | 10 | 32 |
| T1 | Infected + oral treatment | 800 | F2 | 10 | 32 |
| T2 | Infected + oral treatment | 400 | F1 | 10 | 32 |

On day 11 post-infection, the first mortality in fish of the infected control tank (C3) was observed.

The "infected fish" died along from day 11 to day 17 post-intraperitoneal infection and affected to the fish of tanks C3, T1 and T2.

The "uninfected fish" died between day 22 and day 28-post infection and affected to the fish of tanks C2, C3 and T2.

This distribution of mortality turned out interesting because it was clearly separated into two stages. The fish that died first were the ones infected intraperitoneally and later the fish that were infected by cohabitation. This last one happened in the tanks C3 and T2.

After 10 days of oral treatment, the fish were kept in their designated tanks until the 30 day post-intraperitoneal infection, after which all surviving fish of the test were sacrificed.

Figure 5:
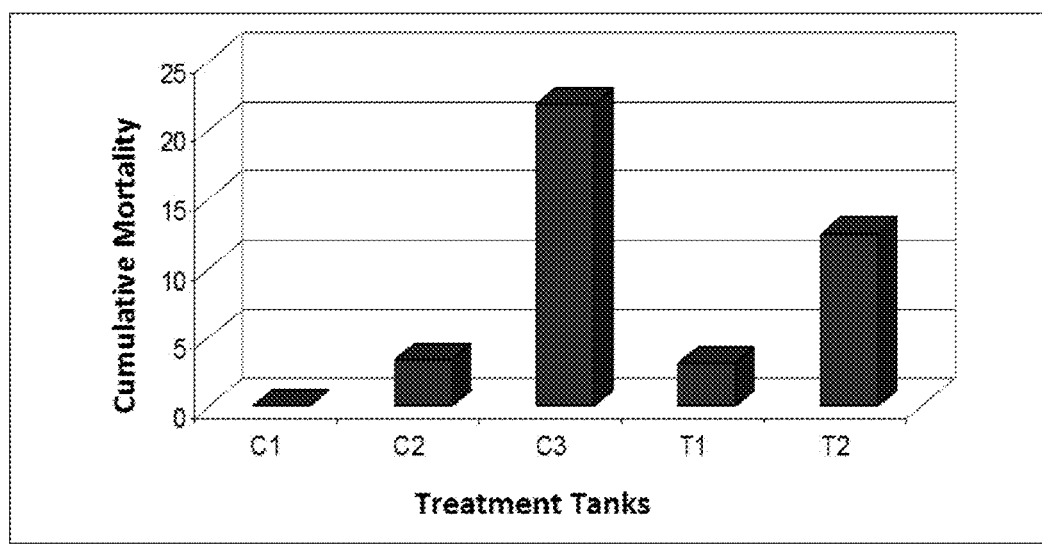
Figure 6:
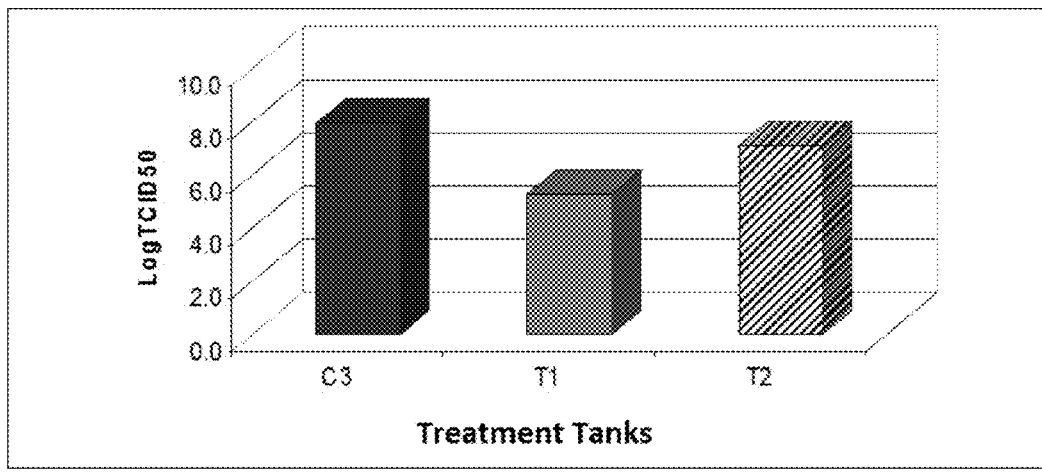
Figure 7:
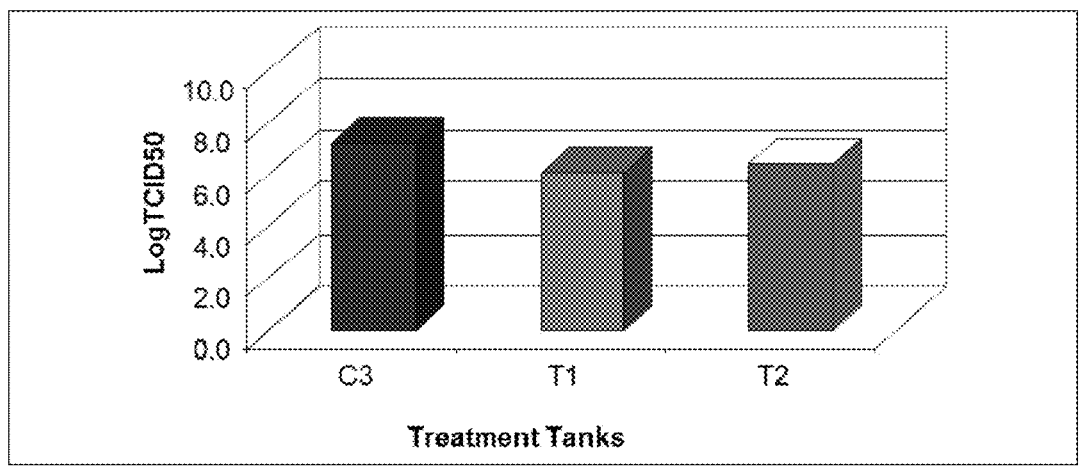
Figure 8:
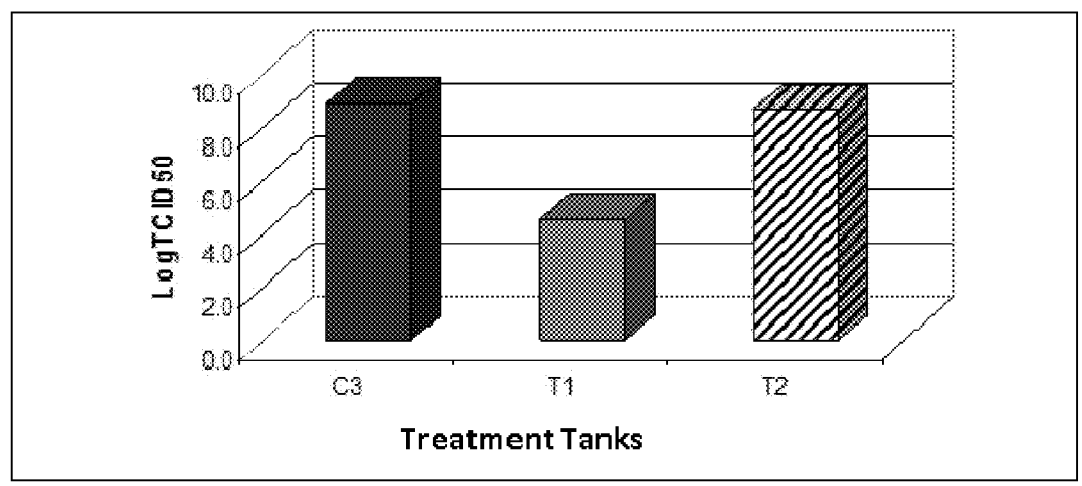

Cumulative mortality observed in the 30 days of the assay is plotted in FIG. 5, which clearly shows that the C3-infected control with no treatment (positive control) was the one presenting the highest mortality rate reaching 21.9%.

In the control tank C1, which was not infected and not treated (negative control), no deaths were observed throughout the study period. Whereas in C2 control were not infected but received a dose of 1600 μg/kg, a cumulative mortality of 3.33% was found.

In the tank where fish were infected and received a dose of 400 μg/kg of antiviral (T2), fewer deaths than in the tank infected and untreated (C3) were observed, reaching 12.5% of mortality. The lowest mortality observed throughout the assay in infected fish was in the tank T2 which received 800 μg/kg of antiviral, reaching a rate of only 3.1%.

These results show evidence that there was a clear development of the disease and that it was effectively controlled with the administration of the antiviral.

Mortality levels expressed with different treatments showed a dose-response effect where the infected untreated tank showed the highest mortality (C3). The tank treated with the lowest dose of the antiviral (T2) had lower mortality than the untreated (C3), however it is still high and it is upper than the higher dose treatment (T1). The tank treated with the highest dose, however, had the lowest mortality (T2) and this is similar compared with the mortality of the controls.

With the control C1 the excipient safety is demonstrated. With control C2 the product safety is demonstrated when using a dose two to four times greater than those used in fish infected with ISAV.

These results show that it would be feasible to use even higher doses for the treatment of infected fish, although with the concentrations studied a really surprising effect is observed.

ISA Diagnosis

Heart tissue was used as sample for the diagnosis of disease. It was stored in absolute ethanol or RNA later, if it were not immediately processed.

Molecular diagnosis was performed using RT-PCR in real time for ISA.

Presumptive diagnosis was performed by evaluation of clinical signs.

All analyzed fish samples from tanks C1 and C2 were negative for the presence of ISA virus. Thus, it was confirmed that the healthy controls not were clinically diseased by ISA, were negative for specific molecular diagnostic tests for the virus. It can be stated therefore, that there was no cross-contamination between infected and uninfected tanks.

Determination of Viral Load

Segment 8 of the virus genome was used to quantify the number of copies of ISAV. The protocols are based on the description of Munir and Kibenge, *Detection of infectious salmon anemia virus by real-time RT-PCR. J. Virol. Meth.* 117, 37-47, 2004.

These results were expressed as TCID50 from the English 50% Tissue Culture Infective Dose, i.e. the amount of pathogen agent (in this case ISA virus) that is capable of producing pathological changes or cytopathic effect in 50% of the inoculated cells.

FIGS. 6-10 show the viral loads of fish subjected to treatments in tanks C3, T1 and T2. As shown in FIG. 6, the average viral load in fish of the tanks T1 and T2 treated with the antiviral, was smaller than the uninfected fish and its magnitude was inversely proportional to the used dose.

Viral load in live fish was very similar in the two treatment tanks T1 and T2 (FIG. 7), and only slightly smaller than that of untreated infected fish (C3). In contrast, in the dead fish (FIG. 8) viral load was significantly lower in fish treated with the highest dose of the antiviral (T1), compared with those that received the lowest dose (T2) and the ones with no treatment (C3). These results are consistent with the higher mortality rate observed in T2 and C3 groups.

Similarly, in infected fish (FIG. 9) the viral load was lower in the fish treated with the highest dose of the antiviral (T1), while the viral loads for fish treated with the lowest doses (T2) and the untreated (C3) were practically the same.

With the treatment of 800 μg/kg of Antiviral no mortality was observed in fish that cohabitated, but the infection was confirmed because viral loads were detected, as shown in FIG. 10 (T1). In the treatment with 400 μg/kg a slightly higher viral load was observed in intraperitoneally uninfected fish (T2 in FIG. 10) and it showed that they were finally infected by cohabitation with those infected.

Viral loads of treated fish (T1 and T2) were in all cases lower than that of the untreated fish (C3) and it was dose dependent.

Necropsies Analysis

The necropsy of the fish in the assay of controlled environment was made through external and internal clinical analysis, with registration of morphometric parameters, description and registration of pathological features (necropsy itself), sampling of internal organs (heart, kidney, spleen and gills) in ethanol and RNA later, with counter samples (i.e. duplication of the samples of the organs same), along with the sample of muscle locket with skin to be used afterwards in analysis of deficiency (presence of the Antiviral in the muscle).

Heart samples of each fish were processed for the viral load analysis; the remaining samples were stored at −80° C.

For purposes of nomenclature, 'live fish' is referred to the situation when the fish is taken alive but must be euthanized for delivery to the laboratory, and 'dead fish' is referred to mortality for ISA virus.

The fish were subjected to necropsy process mostly within 24 hours post sampling.

At the end of the assay all fish were euthanized and necropsied.

As shown in FIGS. 11A and 11B, control fish of tanks C1 and C2 showed normal anatomic pathologic characteristics as well as gills with normal coloration. Internal organs such as liver, spleen and kidney were visualized as normal without inflammation. The coloration of visceral fat was whitish, showing normality.

Similarly, fish of the control tank C2 showed normal anatomic pathologic features (FIGS. 12A and 12B) even FIG. 12 B shows a fish with the stomach full of food, indicating a fish with appetite and high probability of good health.

All fish sampled from tanks C1 and C2 were negative for ISAV molecular analysis.

FIG. 13 shows a fish infected with ISAV that did not received a treatment (tank C3). On day 11 of post intraperitoneal infection this first death occurred for this control. This fish showed characteristic clinical signs of ISA, that is dark burgundy liver with different shades of dark red, which corresponds to liver bleeding and hemorrhage in visceral fat usually as petechial (bleeding in point), within the most distinctive. FIG. 13B is the close-up picture of FIG. 13A.

FIGS. 14 and 15 show infected fish subjected to treatment with the antiviral from tanks T1 and T2. In general they presented mild inflammatory signs.

FIG. 15 A shows a fish from tank T2 that developed ISA and it was subjected to treatment with antiviral. It is noted that it has a stomach with abundant food, the liver looked red but its aspect was closer to normal. It is likely that this fish had been in a recovery process.

It was observed that at necropsy samples of "live" fish, the anatomic pathological findings were less severe, contrary to what was found in autopsies of "dead" fish samples, where fish showed severe clinical signs of ISA.

All analyzed mortality showed clinical signs of ISA, which were more evident in fish that developed the disease for a longer period of time, i.e. those that were infected into the peritoneum respect to those infected by cohabitation. This might have been a result due to increased contact time with the virus.

In general the consumption of food was moderate, however, from day 21 post viral infection, an absence of food in the stomach of all fish sampled is evidenced (controls and treated). The previous day was the last day of treatment and therefore the administration of medicated feed with either excipient or with antiviral. This means that all fish were subjected to a change in their feeding, which requires a period of adaptation.

Evaluation of the Hematocrit

The fish hematocrit was determined for fish that remained alive in each treatment. It was found that the hematocrit always went down in moribund fish no matter what the death cause was.

As discussed, the anatomic pathologic findings were more severe at necropsy samples of fish "dead" than the ones "alive". It is therefore possible that the hematocrit of living samples could not be a definitive indicator for predicting ISA, but it actually is an important parameter for assessing the toxicity of the antiviral used.

The hematocrit normal value in salmon is fairly wide-ranging but a minimum of 44% and a maximum of 64% can be used as limits (according to information obtained from the Universidad Austral of Chile).

Figure 16:
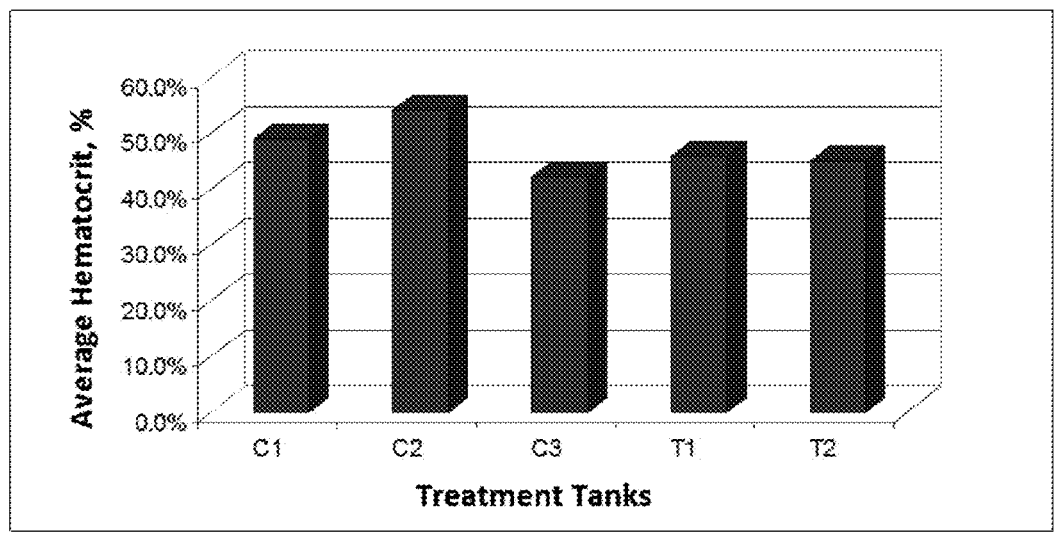

As seen in FIG. 16, the average hematocrit for fish in tanks C1 and C2 was normal and similar from each other, with values close to 50%. These fish were the healthy controls, i.e. not infected with ISA virus.

The difference between C1 and C2 is given by the fact that the fish from tank C2 received a dose of 1600 μg/mL of Antiviral, whereas the fish from the tank C1 did not receive the Antiviral but only the food with the excipients. It was noted that the control fish (C2) receiving the antiviral, showed a slightly upper hematocrit, 54%.

It is remarkable that the fish receiving a high dose of Antiviral, a compound characterized by its production of hemolytic anemia, showed no signs of developing anemia; on the contrary, their hematocrit remained at normal levels (C2).

The hematocrit value of blood samples of the fish from tank C3, which were infected with ISAV and did not receive the Antiviral, showed an average value of 42.1%. This leads to the idea that the hematocrit value may be declining in live fish due to the anemia caused by viral infection.

Hematocrit values of fish from tanks T1 and T2, which were infected with ISAV and were given doses of 800 and 400 μg/mL, respectively, showed values close to 45%, similar to each other and in turn within the normal range described. These values are, on average, higher than that observed in infected fish that did not receive the treatment (C3), which allows us to suggest that treatment with the antiviral would be producing a slight increase in the hematocrit value, a sign of improvement in the fish.

These results are truly amazing since, as mentioned earlier, it has been officially reported in international regulatory agencies that products containing ribavirin for human administration can produce hemolytic anemia; and on the other hand the disease caused by the ISA virus is characterized by showing severe anemia. That is, by no means the effects found in the present invention could have been predicted.

The necropsies showed that the signs of the disease appear to be less severe in the treated fish and that the hematocrit results are slightly lower in untreated fish.

The results allow concluding that treatment with the antiviral compound significantly reduced mortality and even though it did not prevent the viral infection of cohabiting fish, it did decrease their viral loads and signs of the disease, allowing them to stay alive, active and being fed even in the presence of the virus.

Evaluation of the Antiviral Effect of Ribavirin in Harvest Fish

A cage of 107 fish ready for harvest was available; their weight was about 2.5 kg each, to be treated by injection. These fish were naturally infected with ISA virus, which was verified by RT-PCR analysis, and also because they showed evident signs of the disease caused by ISAV and because they were not eating.

In order to ensure that fish received the antiviral treatment and to evaluate whether the compound produced a lowering of the viral load, it was decided to inject the compound intraperitoneally, despite the management stress that this could cause.

On Day 0, 22 fish died and the treatment for the 85 surviving fish was started on Day 1.

The injection was prepared daily by mixing the Antiviral with sterile water in amounts related to the number of needed injections. The fish were intraperitoneally injected with a volume of 200 uL by 10 days, as indicated in Table 3.

TABLE 3

Scheme of the fish intraperitoneal administration

| Cage | Dose | Formulation | N° of fish | Route of administration |
|---|---|---|---|---|
| A | 400 μg/Kg | 1 mg/200 μl | 85 | Injectable |

For monitoring of the internal signs (necropsies) and of the viral load, a sampling was performed every two days, starting on day one and throughout the whole treatment period. This was done using the heart of the fish. Daily mortalities occurred.

Figure 17:
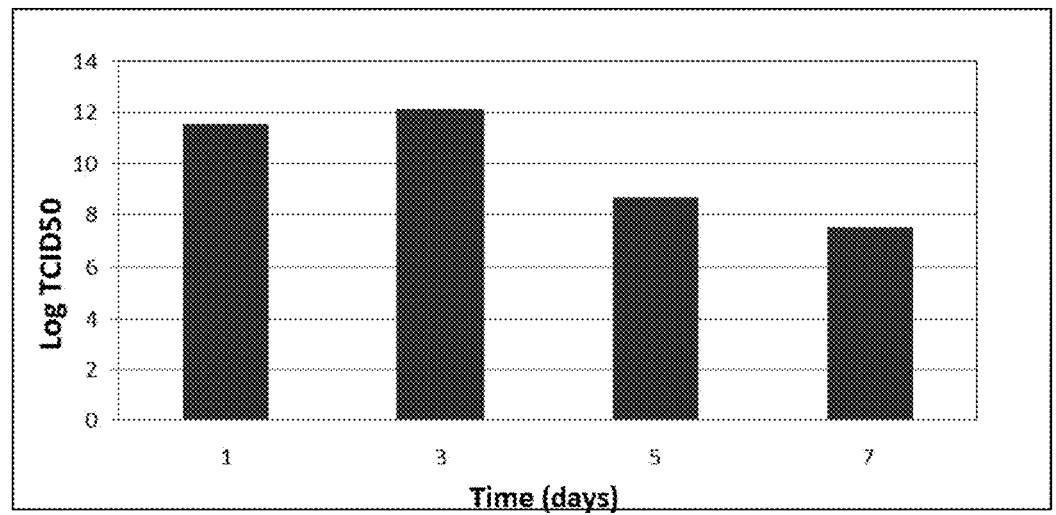

The results of the viral load reflected a downward trend as the treatment days progressed (FIG. 17). This was observed despite the stress caused by the injection procedure.

There was also a slight improvement observed in the condition of the analyzed organs during necropsies.

As shown in FIG. 18, before starting treatment (day 0) the mortalities were about 20% per day and with Antiviral treatment they lowered to 5% in average, until reaching on day 13$^{th}$ the record of just one death per day, which represented 2.7%.

In summary, a decrease of mortality was observed each day as fish received intraperitoneal Antiviral treatment, from the first day of treatment. There was also a slight drop in viral load and an improvement in the necropsies.

Figure 9:
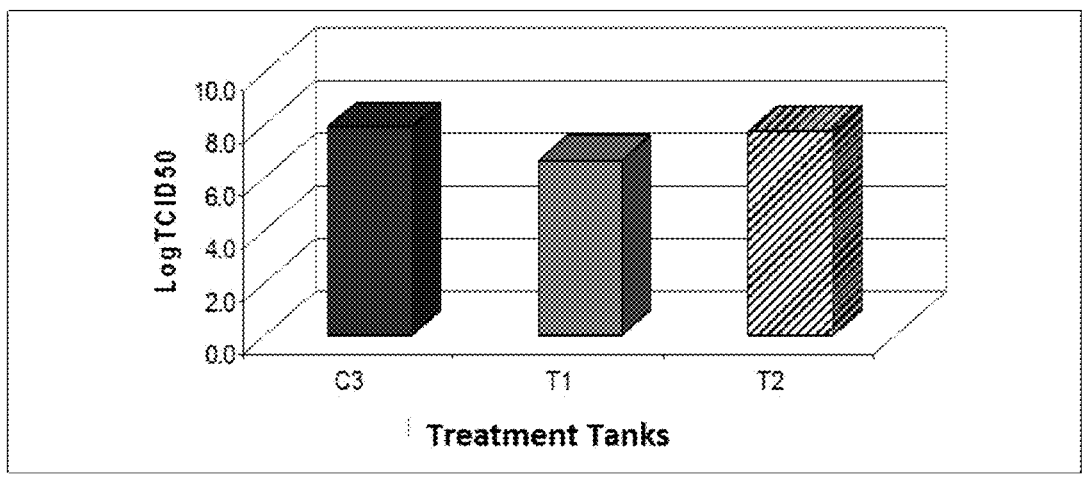
Figure 10:
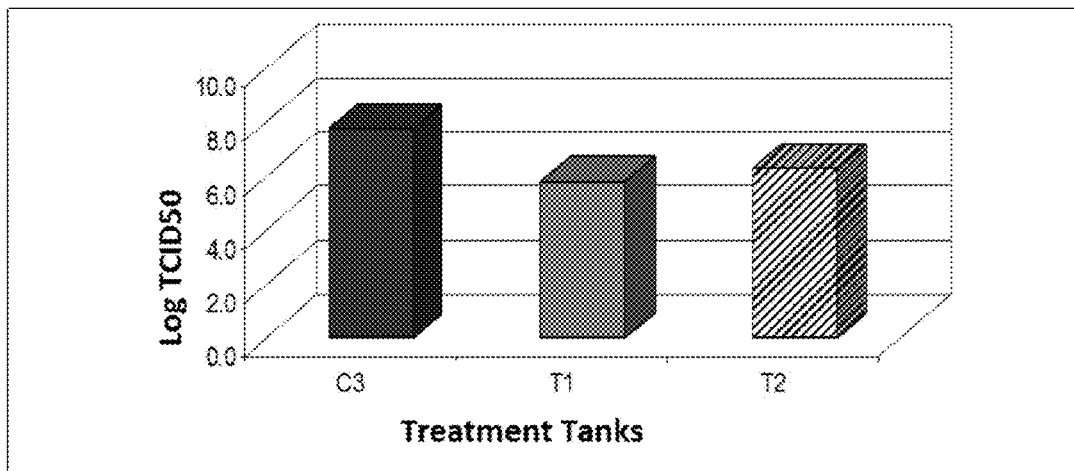
Figure 11A:
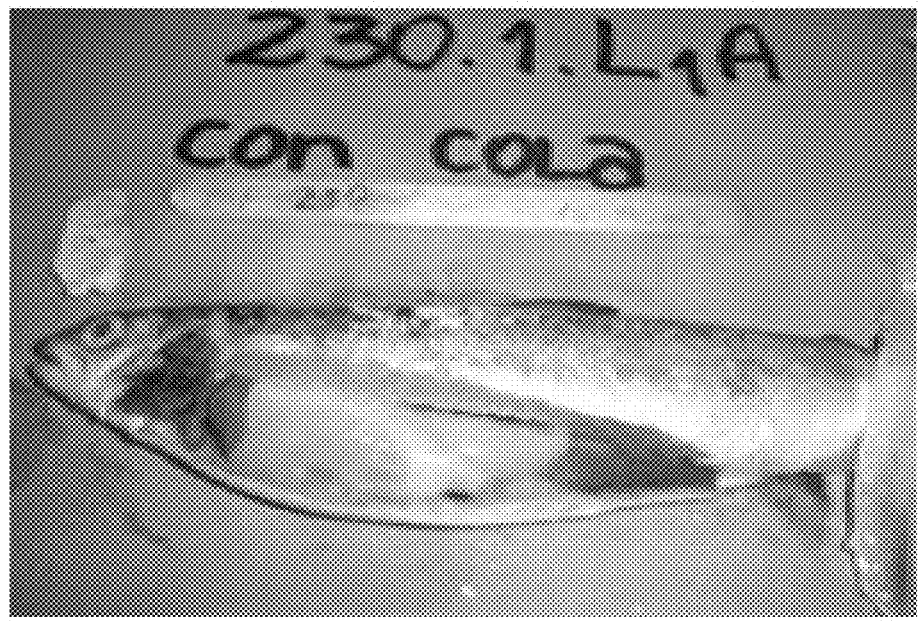
Figure 11B:
Figure 12A:
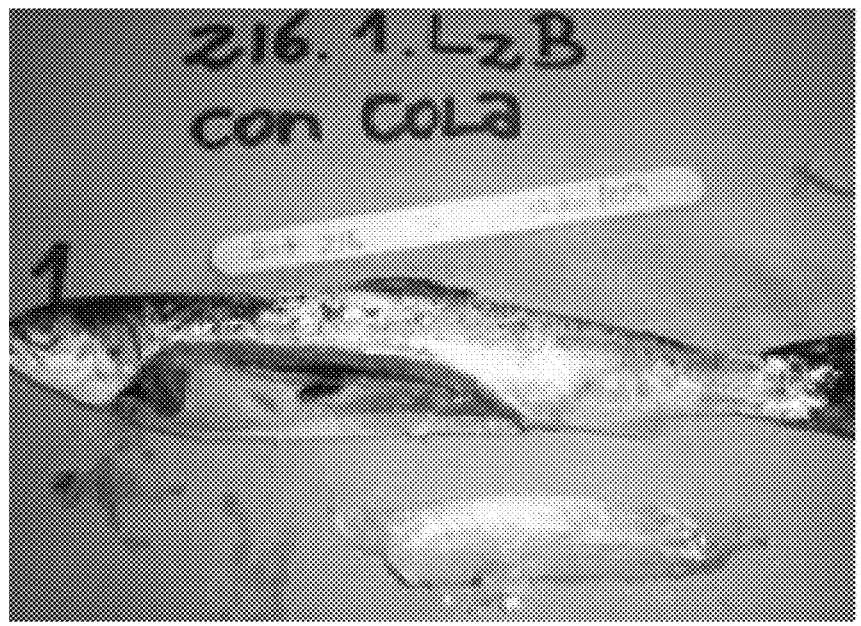
Figure 12B:
Figure 13A:
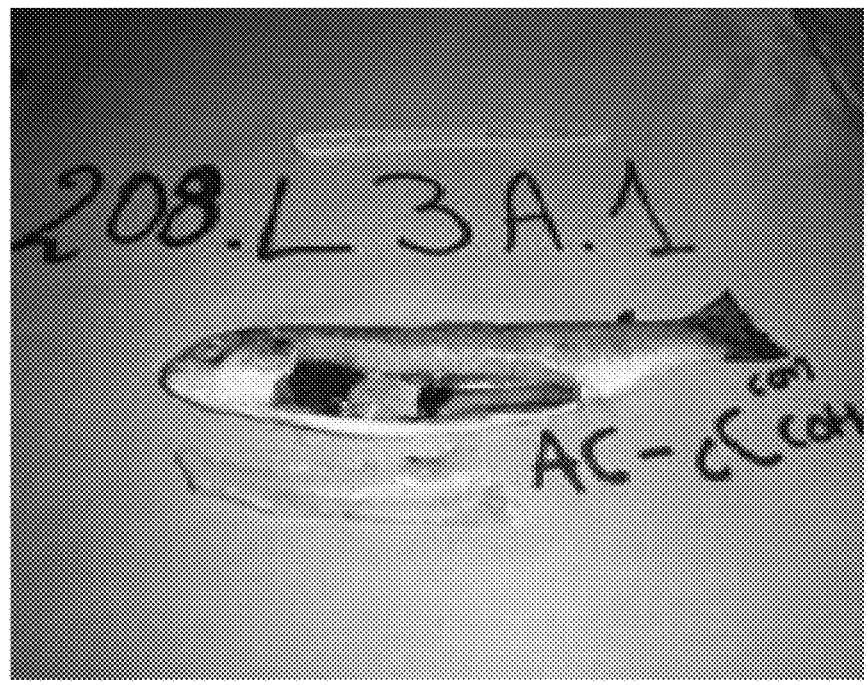
Figure 13B:
Figure 14A:
Figure 14B:
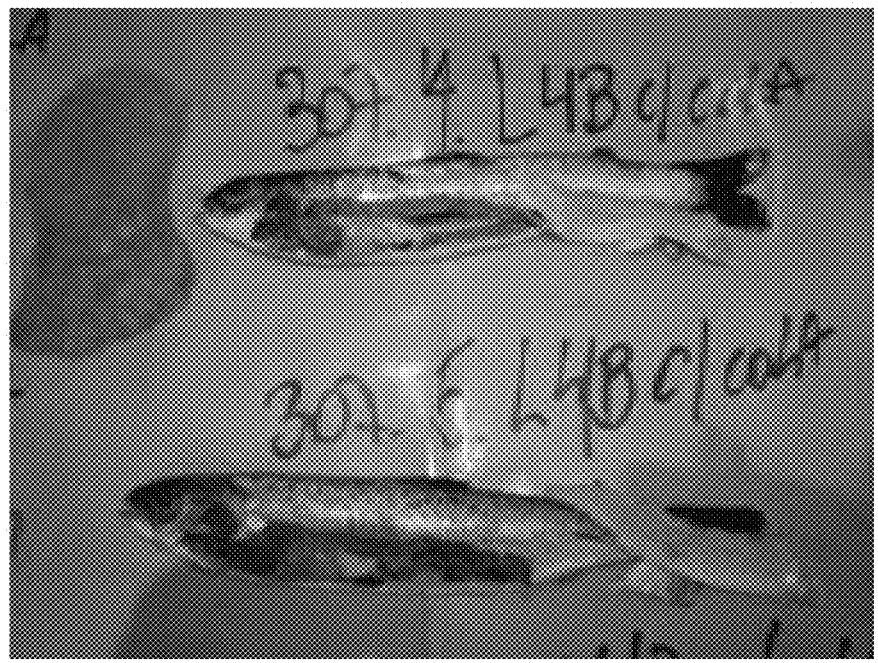
Figure 15A:
Figure 15B:
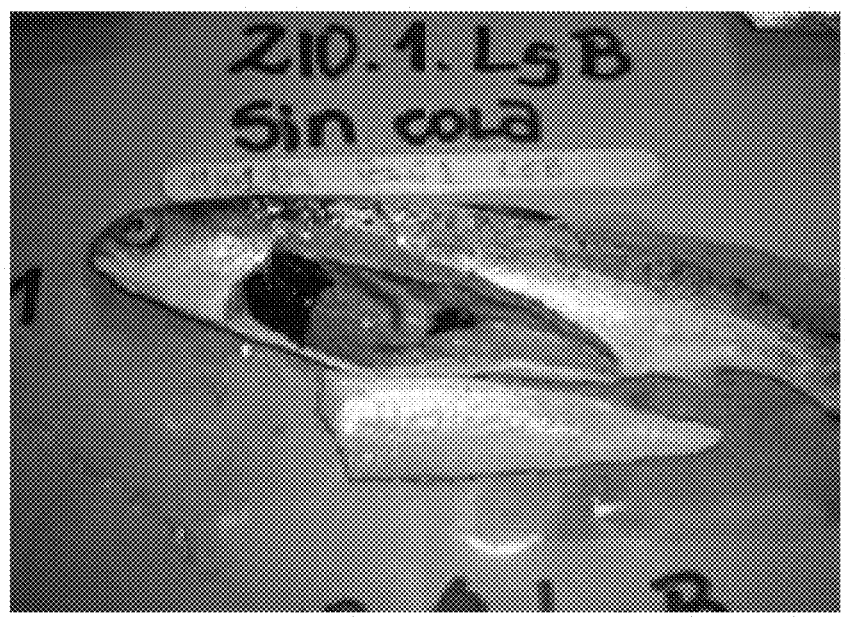

It is worth to notice that these fish were already at a final stage of infection, as proved by the severe damage observed at necropsies and with the high viral loads found (FIG. 17). These were significantly higher than those observed in experimental infection (FIG. 9).

According to this it would be advisable to start treatment as soon as a positive diagnosis for ISAV is obtained, thus achieving even better results, although tests submitted showed that treatment reduced mortality, the viral loads and stopped the damage observed in internal organs.

The invention claimed is:

1. A method of treating infectious salmon anemia (ISA) in salmonids, comprising administering 1-beta-D-ribofuranosyl-1H-1,2,4-triazole-3-carboxamide to the salmonids.

2. The method according to claim 1, comprising oral administration of 1-beta-D-ribofuranosyl-1H-1,2,4-triazole-3-carboxamide to the salmonids.

3. The method according to claim 1, comprising intraperitoneal administration of 1-beta-D-ribofuranosyl-1H-1,2,4-triazole-3-carboxamide to the salmonids.

4. The method according to claim 1, wherein the 1-beta-D-ribofuranosyl-1H-1,2,4-triazole-3-carboxamide is mixed with fish food pellets.

5. The method according to claim 1 comprising administering a medicament comprising 0.5 to 5% of 1-beta-D-ribofuranosyl-1H-1,2,4-triazole-3-carboxamide to the salmonids.

* * * * *